United States Patent [19]

Rossignol et al.

[11] 3,950,351

[45] Apr. 13, 1976

[54] NEW DERIVATIVES OF 2-BENZAMIDO-5-NITRO THIAZOLES

[75] Inventors: Jean-Francois Rossignol, Paris; Raymond Cavier, Villejuif, both of France

[73] Assignee: S.P.R.L. Phavic, Mouscron, Belgium

[22] Filed: Aug. 8, 1974

[21] Appl. No.: 495,749

[30] Foreign Application Priority Data

Aug. 8, 1973 United Kingdom............... 37608/73

[52] U.S. Cl. ........................... 260/306.8 R; 424/270
[51] Int. Cl.² ............... C07D 277/44; C07D 277/58
[58] Field of Search ............... 260/306.8 D, 306.8 R

[56] References Cited
UNITED STATES PATENTS

| | | | |
|---|---|---|---|
| 2,401,522 | 6/1946 | Stoll et al. | 260/306.8 R |
| 2,735,798 | 2/1956 | Kupferborg et al. | 260/306.8 R |
| 2,829,084 | 4/1958 | O'Neill et al. | 260/306.8 R |
| 3,475,446 | 10/1969 | Capps | 260/306.8 R |

FOREIGN PATENTS OR APPLICATIONS

| | | | |
|---|---|---|---|
| 497,537 | 11/1953 | Canada | 260/306.8 D |
| 577,418 | 5/1946 | United Kingdom | 260/306.8 D |
| 1,306,603 | 9/1962 | France | 260/306.8 D |

Primary Examiner—Richard J. Gallagher
Assistant Examiner—Mary Vaughn
Attorney, Agent, or Firm—Sughrue, Rothwell, Mion, Zinn & Macpeak

[57] ABSTRACT

The new derivatives of 2-benzamido-5-nitro-thiazole represented by the formula:

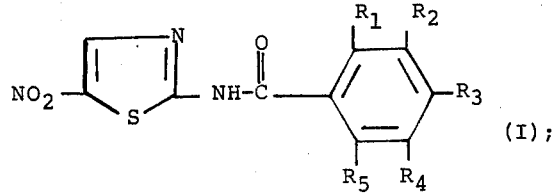

in which at least one of the symbols $R_1$, $R_2$, $R_3$, $R_4$ and $R_5$ represents an acyloxy group, preferably an acetoxy or propionoxy group, whereas the remaining symbols represent hydrogen or one of said remaining symbols represents an alkoxy group, such as the methoxy group, or a halogen atom, such as a chlorine or bromine atom, are interesting parasiticides, fungistatic and molluscicidal agents.

3 Claims, No Drawings

NEW DERIVATIVES OF 2-BENZAMIDO-5-NITRO THIAZOLES

SUMMARY OF THE DESCRIPTION

This invention relates to new derivatives of 2-benzamido-5-nitro-thiazole.

The new derivatives of 2-benzamido-5-nitro-thiazole according to this invention may be represented by the following formula:

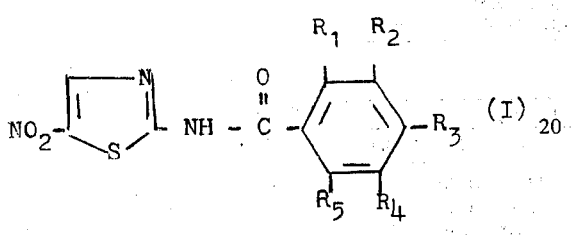

in which at least one of the symbols $R_1$, $R_2$, $R_3$, $R_4$ and $R_5$ represents an acyloxy group, whereas the remaining symbols represent hydrogen or one of said remaining symbols represents an alkoxy group or a halogen atom.

This invention relates also to a process for preparing the new compounds of formula (I), as well as compositions containing at least one of said compounds, as active parasiticidal, fungistatic and/or molluscicidal ingredient.

DETAILED DESCRIPTION OF THE INVENTION

The prepared derivatives of 2-benzamido-5-nitro thiazole of the formula (I) are those in which the acyloxy group is an acetoxy or propionoxy group, whereas the alkoxy group is the methoxy group and the halogen is chlorine or bromine.

The new compounds of formula I are prepared, according to this invention, by reacting 2-amino-5-nitro-thiazole of the formula:

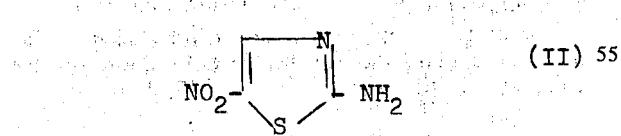

with a benzoyl halide of the formula

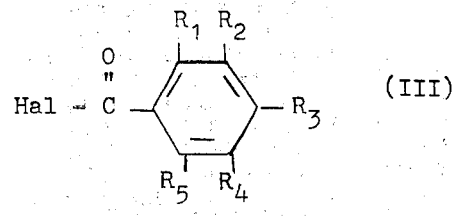

in which Hal represents a halogen atom, preferably a chlorine atom, whereas $R_1$, $R_2$, $R_3$, $R_4$ and $R_5$ have the above meanings, in the presence of triethylamine.

The reaction between the 2-amino-5-nitrothiazole of formula (II) and the benzoyl halide of formula (III) is preferably carried out by adding slowly triethylamine to a stirred solution of the compounds of formulae (II) and (III) in anhydrous tetrahydrofuran, by stirring the reaction mixture and by pouring it in distilled water, the stirring being continued until the desired product crystallizes.

It has been found that the compounds of formula (I) may be used as parasiticides (namely for the control of *Trichomonas vaginalis; Entamoeba dysenteriae; Syphacia obvelata; Hymenolepis nana*, etc.), fungistatic agents and molluscicidal agents.

This invention therefore also relates to compositions to be used for the control of parasites, fungi and molluscs, said compositions containing at least one compound of formula (I), together with a suitable pharmaceutical carrier.

EXAMPLES

The compounds listed in Table I have been prepared by the following method:

To a solution containing one mole of a benzoyl chloride of formula (III) and one mole of carefully purified 2-amino-5-nitro-thiazole in 200 ml of anhydrous tetrahydrofuran, one mole of triethylamine has been slowly added (about 10 minutes) while stirring. The reaction mixture, which became slightly warm, was stirred during 45 minutes and then poured under agitation, into 2 liters of distilled water. The stirring was continued until the precipitation of the desired compound was complete. The obtained precipitate was dried, washed with water, dried again and recrystallized from methanol.

The yields of the desired compounds are between about 55 and 70%.

TABLE I

| Code Number | Substituents in formula I | Melting point °C | Formula | Mol. weight |
|---|---|---|---|---|
| PH 5776 | $R_1$=O—COCH$_3$; $R_2$=$R_3$=$R_4$=$R_5$=H | 202 | $C_{12}H_9N_3O_5S$= | 307 |
| PH 6049 | $R_1$=O—COC$_2$H$_5$; $R_2$=$R_3$=$R_4$=$R_5$=H | 157 | $C_{13}H_{11}N_3O_5S$= | 321 |

TABLE I-continued

| Code Number | Substituents in formula I | Melting point °C | Formula | Mol. weight |
|---|---|---|---|---|
| PH 6045 | $R_1=R_3=R_4=R_5=H; R_2=O-COCH_3$ | 193 | $C_{12}H_9N_3O_5S=$ | 307 |
| PH 6046 | $R_1=R_2=R_4=R_5=H; R_3=O-CO-CH_3$ | 244 | $C_{12}H_9N_3O_5S=$ | 307 |
| PH 6056 | $R_1=R_4=O-COCH_3; R_2=R_3=R_5=H$ | 240 | $C_{14}H_{11}N_3O_7S=$ | 365 |
| PH 6058 | $R_1=R_3=O-COCH_3; R_2=R_4=R_5=H$ | 165 | $C_{14}H_{11}N_3O_7S=$ | 365 |
| PH 6059 | $R_1=R_5H; R_2=R_4=OCH_3; R_3=O-COCH_3$ | 222 | $C_{14}H_{13}N_3O_7S=$ | 367 |
| PH 6057 | $R_1=O-COCH_3; R_2=R_3=R_5=H; R_4=Cl$ | 173 | $C_{12}H_8N_3O_5SCl=$ | 341.5 |
| PH 6103 | $R_1=O-COCH_3; R_2=R_3=R_5=H; R_4=Br$ | 187 | $C_{12}H_8N_3O_5SBr=$ | 386 |
| PH 6161 | $R_1=R_3=R_5=H; R_2=R_4=O-COCH_3$ | 211 | $C_{14}H_{11}N_3O_7S=$ | 365 |
| PH 6162 | $R_1=R_4=R_5=H; R_2=R_3=O-COCH_3$ | 206 | $C_{14}H_{11}N_3O_7S=$ | 365 |
| PH 6177 | $R_1=R_5=H; R_2=R_3=R_4=O-COCH_3$ | 243 | $C_{16}H_{13}N_3O_9S=$ | 423 |
| PH 6196 | $R_1=R_4=R_5=H; R_2=OCH_3; R_3=O-COCH_3$ | 236 | $C_{13}H_{11}N_3O_6S=$ | 337 |
| PH 6239 | $R_1=R_2=O-COCH_3; R_3=R_4=R_5=H$ | 191 | $C_{14}H_{11}O_7N_3S=$ | 393 |

ANALYSIS

| | CALCULATED | | | | | FOUND | | | | |
|---|---|---|---|---|---|---|---|---|---|---|
| | C | H | N | S | Hal | C | H | N | S | Hal |
| PH 5776 | 46.94 | 2.95 | 13.69 | 10.44 | | 47.03 | 3.03 | 13.57 | 10.60 | |
| PH 6049 | 48.59 | 3.42 | 13.08 | 9.96 | | 48.63 | 3.30 | 12.90 | 10.02 | |
| PH 6045 | 46.94 | 2.95 | 13.69 | 10.44 | | 47.01 | 2.89 | 13.60 | 10.39 | |
| PH 6046 | 46.94 | 2.95 | 13.69 | 10.44 | | 46.83 | 2.90 | 13.70 | 10.36 | |
| PH 6056 | 46.02 | 3.01 | 11.50 | 8.76 | | 45.86 | 2.92 | 11.36 | 8.62 | |
| PH 6058 | 46.02 | 3.01 | 11.50 | 8.76 | | 45.92 | 2.96 | 11.39 | 8.89 | |
| PH 6059 | 45.77 | 3.54 | 11.44 | 8.71 | | 45.52 | 3.58 | 11.32 | 8.59 | |
| PH 6057 | 42.16 | 2.34 | 12.29 | 9.37 | Cl 10.39 | 41.96 | 2.21 | 12.12 | 9.32 | Cl 10.17 |
| PH 6103 | 37.30 | 2.07 | 10.88 | 8.29 | Br 20.72 | 37.52 | 1.92 | 10.69 | 8.10 | Br 20.51 |
| PH 6161 | 46.02 | 3.01 | 11.50 | 8.76 | | 45.89 | 2.89 | 11.40 | 8.72 | |
| PH 6162 | 46.02 | 3.01 | 11.50 | 8.76 | | 45.87 | 2.97 | 11.58 | 8.64 | |
| PH 6177 | 45.39 | 3.07 | 9.92 | 7.56 | | 45.21 | 2.92 | 9.78 | 7.49 | |
| PH 6196 | 46.29 | 3.25 | 12.46 | 9.49 | | 46.11 | 3.12 | 12.33 | 9.42 | |
| PH 6239 | 49.87 | 2.80 | 10.69 | 8.14 | | 49.75 | 2.68 | 19.72 | 8.11 | |

Biological tests have been performed with a great number of compounds of formula I, using the following techniques: 1)- Test for amoebicidal activity described by R. CAVIER, Ann. pharm. franç. 1960, 18, pages 583–589 and by R. CAVIER and J. CENAC, Bull. Soc. Path. exot. 1972, 65, pages 399–404. 2) - Test for trichomonacidal activity described by R. Cavier and P. BUOT, Ann. Pharm. franç., 1964, 22, pages 211–216 and by R. CAVIER and J. CENAC, Semaine des Hopitaux, 1972, 48, pages 391–394. 3)- Tests for anthelminthics described for nematodes (such as *Syphacia obvelata*) by R. CAVIER, Bull. Soc. Path. exot. 1962, 55, pages 412–417, and for cestodes (such as *Hymenolepis nana*), by R. CAVIER, Ann. pharm. franç. 1956, 14, pages 545–552 and by R. CAVIER and M. J. NOTTEGHEM, Ann. Pharm. franç., 1968, 28, pages 603–606. 4)- Method for determining fungistatic doses:

MEDIUM

A liquid Sabouraud medium having the following composition is used:

| Peptone (Oxoid) | 10 grams |
| Glucose anhydrous | 20 grams |
| Distilled water to make up to | 1,000 ml. |

If necessary, the pH is adjusted to 6.4 and the medium is sterilized.

SOLUBILIZATION of the compounds to be tested

The compounds are dissolved in dimethylformamide to which polyethylene glycol is sometimes added. From the motherliquor, successive diluted solutions are prepared in the liquid Sabouraud medium, so as to obtain concentrations of 1,3, 10, 30, 100 and 300 mg per ml. For the first dilution, one should not add more than 10% of the mother-liquor to the Sabouraud medium. Subsequently 9 ml per tube of the various solutions in the liquid Sabouraud medium are distributed.

Reference tubes corresponding to the highest solvent concentrations are also prepared.

SEEDING

For dermatophites:

Various dermatophyte strains are cultivated on Sabouraud agar medium. Homogeneous suspensions from 1 to 2 months old cultures in the liquid Sabouraud medium are prepared, the obtained suspensions stirred in the presence of glass pearls having a light transmission of about 40%.

One drop of said suspensions is introduced in the tubes containing the various concentrations of the compound to be tested.

For yeasts:

The same method as for dermatophytes, except that 2 to 3 weeks old cultures on Sabouraud agar medium are used.

INCUBATION at 25°C ± 2°C in the dark

READING

Direct reading after 5 days of incubation of yeasts 10 days of incubation for dermatophytes.

Following Table II gives the results of the tests which have been made with various compounds of the formula (I) on a number of parasites.

TABLE II

| Compound Code number | Trichomonas Starting activity | Lethal action | Entamoeba dysenteriae | Syphacia ovelata (1) | (2) | (3) | (4) | Hymenolepis nana (1) | (2) | (3) | (4) |
|---|---|---|---|---|---|---|---|---|---|---|---|
| | | | PARASITICIDAL ACTIVITIES | | | | | | | | |
| PH 5776 | 0.5 to 1.25 | 6 | 100 | 10 | 0 | 6 | 60 | 10 | 0 | 10 | 100 |
| PH 6049 | 50 to 100 | | >100 | 10 | 0 | 2 | 20 | 10 | 0 | 10 | 100 |
| PH 6045 | 50 to 100 | | 10 | 10 | 0 | 0 | 0 | 10 | 0 | 4 | 40 |
| PH 6046 | 50 to 100 | | 10 | 10 | 0 | 2 | 20 | 10 | 0 | 3 | 30 |
| PH 6056 | 50 to 100 | | 100 | 10 | 0 | 1 | 10 | 10 | 0 | 6 | 60 |
| PH 6058 | 50 to 100 | | 100 | 10 | 0 | 2 | 20 | 10 | 0 | 2 | 20 |
| PH 6059 | 0.5 | 50 | 50 to 100 | 10 | 0 | 2 | 20 | 10 | 0 | 1 | 10 |
| PH 6057 | 10 | | 100 | 10 | 0 | 2 | 20 | 10 | 0 | 7 | 70 |
| PH 6103 | 100 | | 10 | 10 | 0 | 2 | 20 | 10 | 0 | 4 | 40 |
| PH 6161 | 50 to 100 | | 100 | 10 | 0 | 7 | 70 | 10 | 0 | 0 | 0 |
| PH 6162 | 50 to 100 | | 100 | 10 | 0 | 2 | 20 | 10 | 0 | 1 | 10 |
| PH 6177 | 100 | | 100 | 10 | 0 | 0 | 0 | 10 | 0 | 0 | 0 |
| PH 6196 | 50 to 100 | | 5 to 10 | 10 | 0 | 0 | 0 | 10 | 0 | 0 | 0 |
| PH 6239 | >100 | | 100 | 10 | 0 | 1 | 10 | 10 | 0 | 2 | 20 |

(1) Number of subjects
(2) Number of dead subjects
(3) Number of subjects from which the parasite has been eradicated
(4) Percentage of activity Tests on *Hymenolepis nana* in mice have also been performed in order to determine the anthelminthic activity of various cmpounds of formula I, according to the technique of R. CAVIER. The compounds to be tested have been administered in a single dose. Four hours later, the animals have been purged by means of sodium sulfate.

The results of these tests are given in the following Table III.

TABLE III

| Compounds Code number | Doses in mg/kg | Number of Treated mice | Mice from which parasite has been eradicated Number | Percentage | Mortality |
|---|---|---|---|---|---|
| PH 5776 | 200 | 10 | 10 | 100 | 0 |
| | 100 | 10 | 10 | 100 | 0 |
| | 50 | 30 | 30 | 100 | 0 |
| | 25 | 20 | 20 | 100 | 0 |
| PH 6049 | 200 | 20 | 20 | 100 | 0 |
| | 100 | 20 | 18 | 90 | 0 |
| | 50 | 20 | 14 | 70 | 0 |
| | 25 | 20 | 8 | 40 | 0 |
| Reference | — | 40 | 2 | 5 | 0 |

The above tests clearly show that the compounds of formula I may be useful for the treatment of various parasitic diseases, such as trichomoniasis, amoebiasis, oxyuriasis and taeniasis, as well as for the treatment of various mycoses.

For the treatment of parasitic diseases, the compounds of formula I may be used together with usual pharmaceutical carriers in tablets, capsules, syrups and gynaecological ovules.

For the treatment of mycoses, the compounds of formula I may be used together with usual pharmaceutical carriers in tablets, capsules, ointments and suppositories.

When used as anthelminthics, tablets containing about 500 mg of a compound of formula I may be administered to adults at a dose of 2 to 4 tablets per day.

The compounds of formula I are also active as molluscicides, namely the molluscs causing schistosomiases.

It has been found that the compounds PH 5776, PH 6049, PH 6057 and PH 6103 are active against *Biomphalaria glabrata* at a dose 1 part per million, whereas the compounds PH 6045, PH 6059 and PH 6239 are active against the same mollusc at a dose of 10 parts per million.

For determining the molluscicidal activity, the following test is used:

Two to four weeks old molluscs are used. Five molluscs having the same size are put in the same container and covered with a testing solution at a temperature of 26°C during 24 hours. After rinsing, the animals are again observed after 24 hours. The total duration of this test therefore is 48 hours.

Testing solutions containing respectively 10, 1 and 0.1 parts per million of the compounds to be tested in water having a hardness of 10° (hydrotimetric) are used.

The sensitivity of the mollusc strain is standardized with known reference molluscicides such as Niclosamide (Registered Trademark).

Toxicity investigations have shown that the compounds of formula I have a very low acute toxicity both on oral administration and on intraperitoneal administration to mice.

The acute toxicity of compound PH 5776 is more than 4000 mg/kg after oral administration to mice and of more than 95 mg/kg after intraperitoneal administration to mice.

What we claim is:

1. A 2-benzamido-5-nitro-thiazole of the formula:

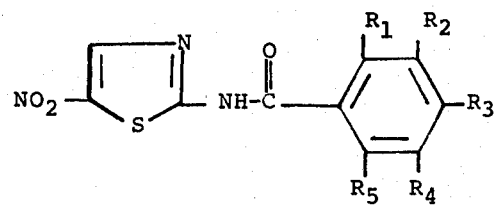

in which one or two of the symbols $R_1$, $R_2$, $R_3$, $R_4$ and $R_5$ represents an acetoxy or propionyloxy group, and the remaining symbols represent hydrogen with the proviso that one of the remaining symbols can represent a methoxy group or a chlorine or bromine atom.

2. 2-(2'-acetoxy)-benzamido-5-nitro-thiazole.

3. 2-(2'-propionyloxy)-benzamido-5-nitro-thiazole.

* * * * *